(12) United States Patent
Wan et al.

(10) Patent No.: US 10,684,300 B2
(45) Date of Patent: Jun. 16, 2020

(54) ROTATING DISC TYPE FECAL OCCULT BLOOD DETECTION ANALYZER

(71) Applicant: W.H.P.M BIORESEARCH AND TECHNOLOGY CO., LTD., Beijing (CN)

(72) Inventors: John Wan, Beijing (CN); Zejiang Li, Beijing (CN); Qingwei Shen, Beijing (CN)

(73) Assignee: W.H.P.M BIORESEARCH AND TECHNOLOGY CO., LTD., Beijing (CN)

( * ) Notice: Subject to any disclaimer, the term of this patent is extended or adjusted under 35 U.S.C. 154(b) by 229 days.

(21) Appl. No.: 15/771,485

(22) PCT Filed: Sep. 29, 2016

(86) PCT No.: PCT/CN2016/100781
§ 371 (c)(1),
(2) Date: Apr. 27, 2018

(87) PCT Pub. No.: WO2017/071450
PCT Pub. Date: May 4, 2017

(65) Prior Publication Data
US 2018/0340950 A1    Nov. 29, 2018

(30) Foreign Application Priority Data

Oct. 30, 2015    (CN) .......................... 2015 1 0726035

(51) Int. Cl.
*G01N 1/00*         (2006.01)
*G01N 35/02*        (2006.01)
*G01N 35/04*        (2006.01)
*G01N 33/483*       (2006.01)
*G01N 35/00*        (2006.01)

(52) U.S. Cl.
CPC ......... *G01N 35/025* (2013.01); *G01N 33/483* (2013.01); *G01N 35/00732* (2013.01); *G01N 35/04* (2013.01); *G01N 2035/00752* (2013.01)

(58) Field of Classification Search
CPC ....................................................... G01N 1/00
See application file for complete search history.

(56) References Cited

FOREIGN PATENT DOCUMENTS

| CA | 2130970 A1 | 3/1995 |
|---|---|---|
| CA | 2 928 521 A1 | 4/2015 |
| CN | 102192996 A | 9/2011 |

(Continued)

*Primary Examiner* — Jyoti Nagpaul
(74) *Attorney, Agent, or Firm* — Scully Scott Murphy & Presser

(57) ABSTRACT

A rotating disc type fecal occult blood detection analyzer is used for detecting sample boxes (16). A sample box (16) comprises a transparent sleeve, and a fecal collector and a test strip provided in the transparent sleeve. The rotating disc type fecal occult blood detection analyzer comprises: a disc-shaped sample box holder (17) carrying multiple sample boxes (16); a driving device for driving the sample box holder (17) to rotate; a pressing device for pressing the sample boxes (16) down; and an information collecting device for collecting color ribbon information presented on the test strips in the sample boxes (16) and label information on the sample boxes (16). The rotating disc type fecal occult blood detection analyzer is small in size and compact in structure It is portable and makes detection more flexible.

10 Claims, 5 Drawing Sheets

(56) References Cited

FOREIGN PATENT DOCUMENTS

| | | |
|---|---|---|
| CN | 102539805 B | 7/2012 |
| CN | 102879592 A | 1/2013 |
| CN | 103063856 B | 4/2013 |
| CN | 104569460 A | 4/2015 |
| CN | 205067507 U | 3/2016 |
| JP | 2004-101292 A | 4/2004 |
| WO | WO 2009/011869 A | 1/2009 |

ROTATING DISC TYPE FECAL OCCULT BLOOD DETECTION ANALYZER

The present invention claims a priority of Chinese patent titled "ROTATING DISC TYPE FECAL OCCULT BLOOD DETECTION ANALYZER", with application number CN2015107260358.

TECHNICAL FIELD OF THE INVENTION

The present invention relates to the field of medical detection, and particularly to a rotating disc type fecal occult blood detection analyzer.

BACKGROUND OF THE INVENTION

"FOB": English abbreviation of fecal occult blood, refers to occult blood in feces, be called fecal occult blood for short, which is slight hemorrhage of the digestive tract. Generally, fecal occult blood does not cause a change in feces color. Erythrocytes are damaged by digestion and there is no abnormal change in feces appearance. Bleeding cannot be confirmed visibly and microscopically. A small amount of blood cells in feces can be discovered only when the feces are tested. A small amount of bleeding for a long time is usually accompanied by anaemic symptom. Since fecal occult blood cannot be discovered directly through eyes, most patients suffering from malignant tumors of the digestive tract at early stages cannot be diagnosed in time and fail to receive early intervening treatment, thus missing the best time for treatment, and fecal occult blood ambushing in people's bodies likes a silent killer.

CN103543285A discloses an automatic fecal occult blood detection device for detecting a sample box. The sample box includes a transparent sleeve, and a feces collector and test strips provided in the transparent sleeve. The detection device includes: a import channel and a export channel are provided in coordination and respectively configured to independently operate for conveying a sample box; a transferring platform is located between the import channel and the export channel; a push rod is configured to push the sample box on the import channel to the export channel by the transferring platform, and an image acquisition device is provided in one side of the export channel, wherein the image acquisition device is configured to acquire color ribbon information presented on the test strips.

The automatic fecal occult blood detection device has the following problems:

The import channel and the export channel are provided in coordination, which increases a floor space of the device.

SUMMARY OF THE INVENTION

The present invention provides a rotating disc type fecal occult blood detection analyzer to solve a problem that an existing automatic fecal occult blood detection device occupies a larger floor space.

For this purpose, the present invention provides a rotating disc type fecal occult blood detection analyzer used for detecting sample boxes. The rotating disc type fecal occult blood detection analyzer comprises:

A disc-shaped sample box holder carrying multiple sample boxes;

A driving device for driving the sample box holder to rotate;

A pressing device for pressing the sample boxes down; and

An information collecting device for collecting color ribbon information presented on the test strips in the sample boxes and label information on the sample boxes.

Further, the sample box holder can rotate about 360 degree, multiple clamping grooves for clamping or carrying sample box are provided in the bottom of the sample box holder, a open window for photographing and scanning the front and back of the sample box is provided above the side of the clamping groove.

Further, the driving device comprises: a driving motor for sample box holder, a gear set is connected to the driving motor for sample box holder, and a principal axis is connected to the gear set, the sample box holder is connected to the principal axis.

Further, the pressing device comprises: stand, a driving motor for pressing is provided in the stand, a press lever is driven by the driving motor for pressing, and a cardinal axis is used for hinging the press lever to the stand.

Further, the information collecting device comprises: a barcode scanning device is provided inside the sample box holder, and a camera is provided outside the sample box holder, the connecting line between the barcode scanning device and the camera is same as the radial direction of the sample box holder.

Further, the pressing device further comprises: a first sensor for detecting the position of the press lever.

Further, the driving device further comprises: a second sensor for detecting the position of the sample box holder.

Further, the sample box holder further provides: a third sensor for detecting whether the sample box is loaded into the sample box holder.

Further, the rotating disc type fecal occult blood detection analyzer comprises: a base plate, the sample box holder, driving device, pressing device and information collecting device are provided in the base plate.

Further, the rotating disc type fecal occult blood detection analyzer further comprises: a controlling device is used for connecting the driving device, the pressing device and the information collecting device.

The present invention adopts a disc-shaped sample box holder for carrying sample boxes, transferring and detecting the sample box are realized by rotating the sample box holder. The problems such as a larger floor space and larger volume raised by the conveyor types of chain type or conveyor belt type existing in an existing automatic fecal occult blood detection device are solved by transferring type of circular type. Thus the present invention is small in size and compact in structure, and it is portable and makes detection more flexible.

The present invention can implement continuous detection and accurate location of a plurality of sample boxes. The sample boxes will not be overturned, and can be pressed accurately. Diluent of fecal samples reacts with test strips so as to complete detection. The result output is realized after collecting the image.

DETAILED DESCRIPTION OF THE EMBODIMENTS

FIG. 2 is a stereoscopic structure schematic diagram of front elevation view of a rotating disc type fecal occult blood detection analyzer according to an embodiment of the present invention, wherein the sample box holder is installed in;

Numerals in the accompanying drawings:

1 motor; 2 small gear; 3 principal axis; 4 a third sensor; 5 locating device, 6 press plate; 7 barcode scanning device; 8 camera; 9 press lever; 10 motor; 11 a first sensor; 12 linkage part; 13 a second sensor; 14 big gear; 15 locating plate; 16 sample box; 17 sample box holder; 20 base plate; 30 stand; 40 support plate.

DETAILED DESCRIPTION OF THE EMBODIMENTS

The present invention will be described with reference to the accompanying drawings in order to understand the technical features, purposes, and effect of the present invention more clearly.

Figure 1:
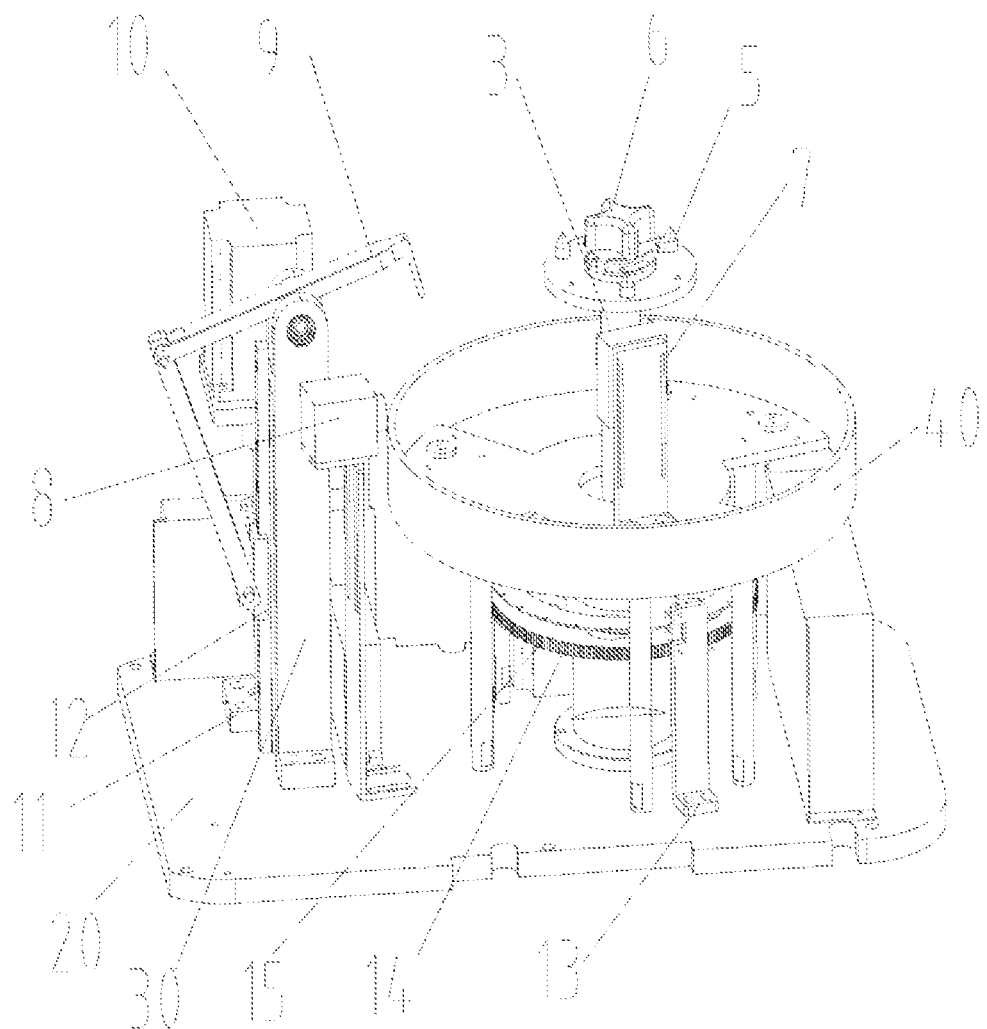
FIG. 1 is a structure schematic diagram of a rotating disc type fecal occult blood detection analyzer according to an embodiment of the present invention, wherein the sample box holder is removed out.
Figure 2:
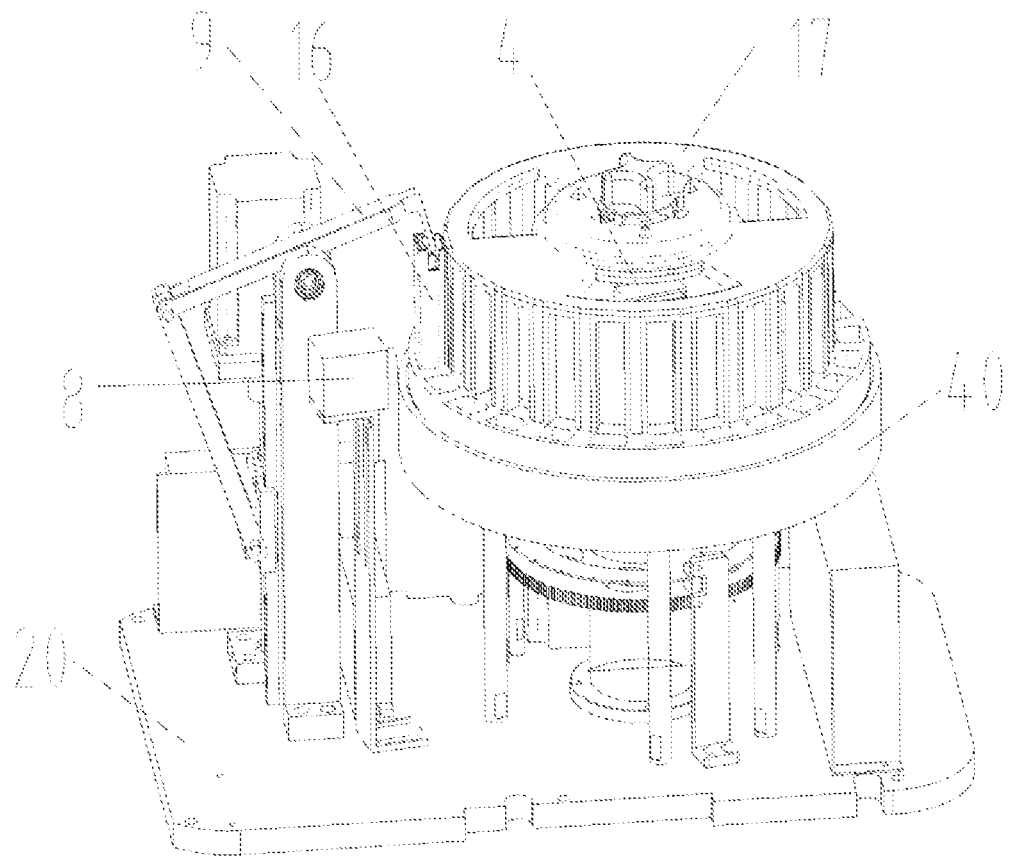
Figure 3:
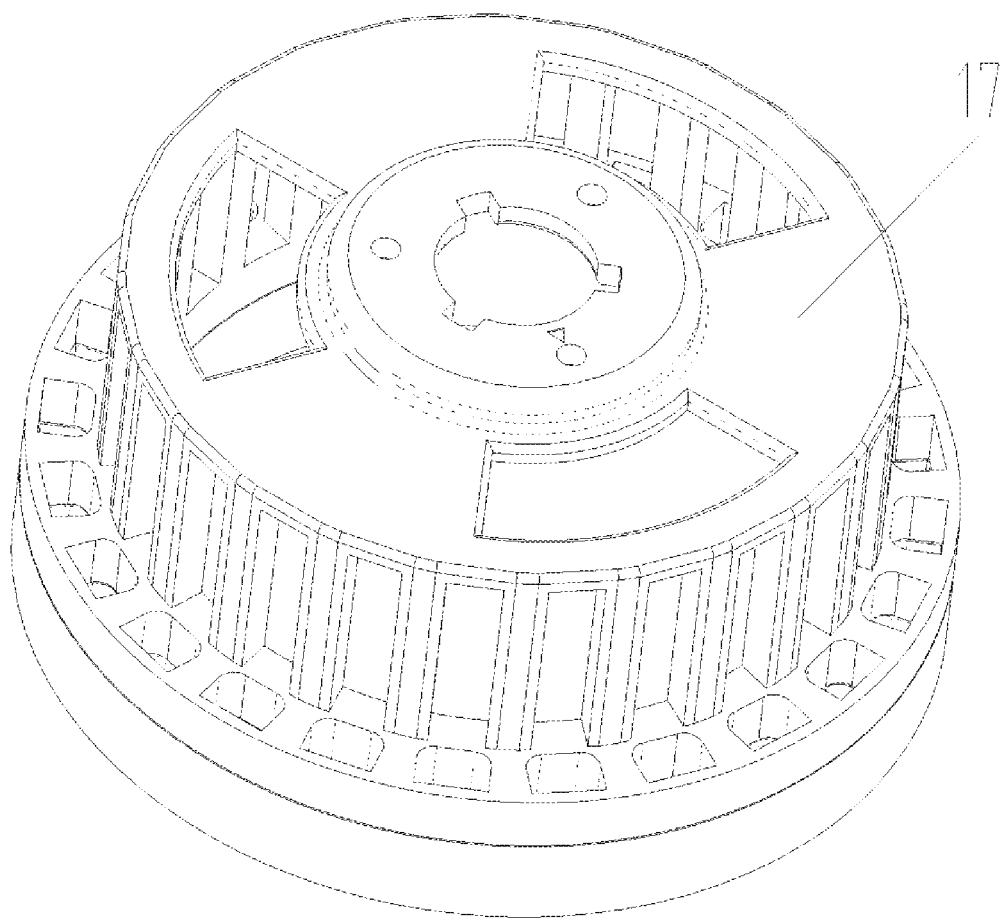
FIG. 3 is a structure schematic diagram of sample box holder according to an embodiment of the present invention.
Figure 5:
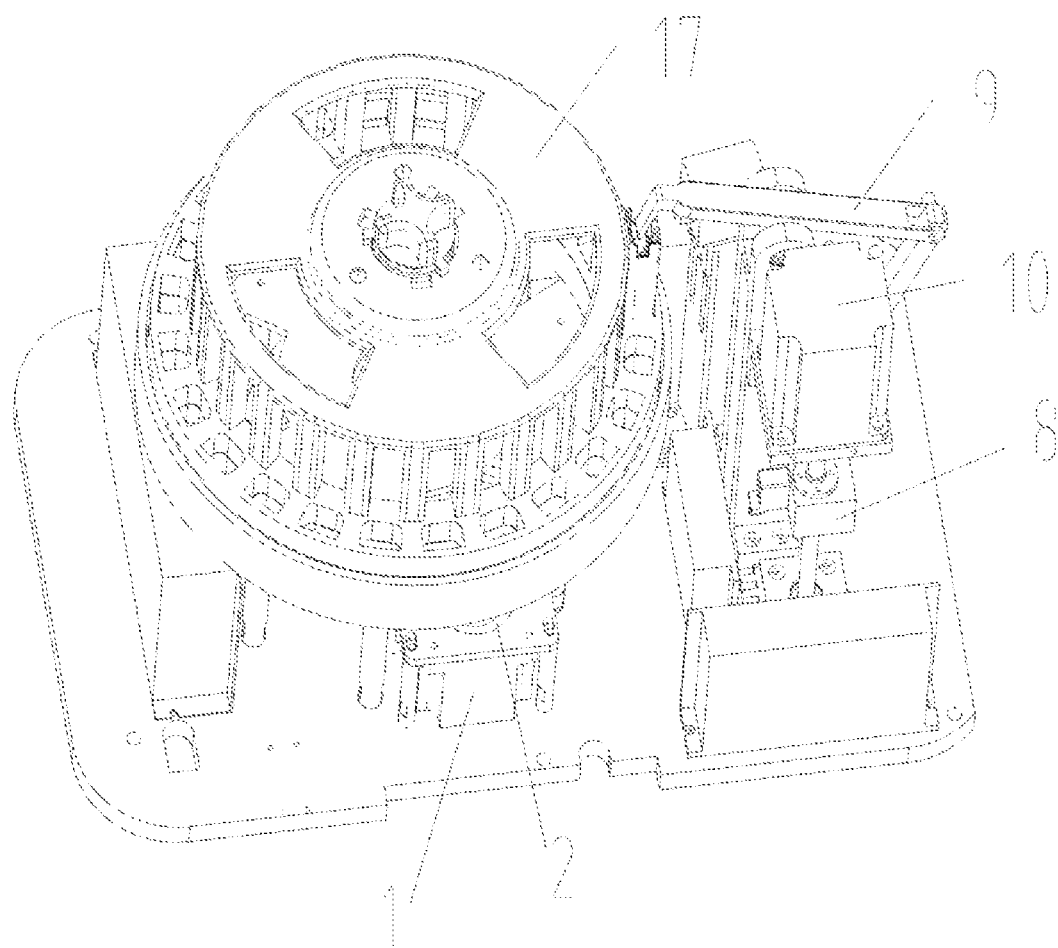
FIG. 5 is a stereoscopic structure schematic diagram of top plan view of a rotating disc type fecal occult blood detection analyzer according to an embodiment of the present invention.

As shown in FIG. 1, FIG. 2 and FIG. 5, a rotating disc type fecal occult blood detection analyzer according to an embodiment of the present invention comprises:

A sample box holder 17 carrying multiple sample boxes is fixed at a principal axis 3. As shown in FIG. 3, the sample box holder 17 is disc-shaped and can rotate about 360 degree. Multiple clamping grooves for clamping or carrying sample box 16 are provided in the bottom of the sample box holder 17, a open window for photographing and scanning the front and back of the sample box 16 is provided above the side of the clamping groove. The sample box holder 17 is used as a platform for the reaction between sample and test strips and for collecting information; the sample box holder 17 is fixed to principal axis by support plate 40, the support plate 40 is disc shape and sleeved to the principal axis. Multiple perforated holes are provided inside the support plate 40, the perforated holes are used for installing parts such as the third sensor 4 and barcode scanning device 7. The support plate 40 supports the sample box holder 17;

A press plate 6 can be provided at top of the sample box holder 17. The press plate 6 reciprocates with respect to the principal axis and cooperates with the sample box holder 17 by specific geometry, so that axial positioning of the sample box holder 17 on the principal axis 3 is realized; the press plate is circular, multiple protruding flanges are evenly provided in outermost edge of the circular press plate. Such flanges are cooperated with rectangular groove on the sample box holder, so that loading, unloading and positioning of the sample box holder 17 are realized;

A driving device for driving the sample box holder 17 to rotate;

A pressing device for pressing the sample boxes 16 in the clamping grooves down; and An information collecting device for collecting color ribbon information shown on the test strips in the sample boxes and label information on the sample boxes (patient information on the sample box).

With respect to the structure and detection principle of sample box, please refer to prior arts such as Chinese utility model patent CN204613211U and Chinese invention patent CN102879592.

Further, as shown in FIG. 1, FIG. 2 and FIG. 5, the driving device comprises: a driving motor 1 for sample box holder, a gear set is connected to the driving motor for sample box holder, and a principal axis 3 is connected to the gear set, the sample box holder 17 is connected to the principal axis 3. The gear set comprises a big gear and a small gear engaged with each other, a driving motor 1 for sample box holder drives the small gear, the small gear drives the big gear to rotate, the spindle of big gear is principal axis or is connected to the principal axis so as to drive the principal axis 3 to rotate, and drive the sample box holder 17 to rotate. A positioning device 5 is provided in the principal axis, such as locating pin, the positioning device is used for fixing and positioning the sample box holder 17 so as to ensure stability of the sample box holder 17 during rotation. The sample box holder 17 runs under specified speed by transmission of the big gear and the small gear by use of the above mentioned driving and transmitting structures, the sample box holder 17 rotates reliably, rotate speed can be controlled so as to meet the speed for detection requirement.

Further, as shown in FIG. 1 and FIG. 2, the pressing device comprises: stand 30, a driving motor 10 for pressing is provided in the stand, a press lever 9 is driven by the driving motor for pressing, and a cardinal axis is used for hinging the press lever to the stand. Thus the press lever 9 can realize reciprocating motion. The driving motor 10 for pressing can connect a linkage part 12 so as to drive the linkage part 12 for reciprocating motion, the linkage part 12 further drive the press lever 9 so as to realize reciprocating motion, wherein the linkage part 12 can be sliding block.

Further, the information collecting device comprises: a barcode scanning device 7 is provided inside the sample box holder, and a camera 8 is provided outside the sample box holder, the barcode scanning device 7 is used for collecting patient information on the sample box, the camera 8 is used for collecting detection result (image or status on strip). The connecting line between the barcode scanning device and the camera is same as the radial direction of the sample box holder, so that the barcode scanning device 7 can collect patient information on the sample box inside the sample box holder, meanwhile the camera 8 can collect detection result outside the sample box holder. Thus barcode scanning and photographing can carried out at the same time so as to quicken the detection speed.

Further, the pressing device further comprises: a first sensor 11 for detecting the position of the press lever, which is used for detecting the press lever and realizing positioning and resetting. The first sensor 11 is such as photoelectric sensor, which can detect rapidly.

Figure 4:
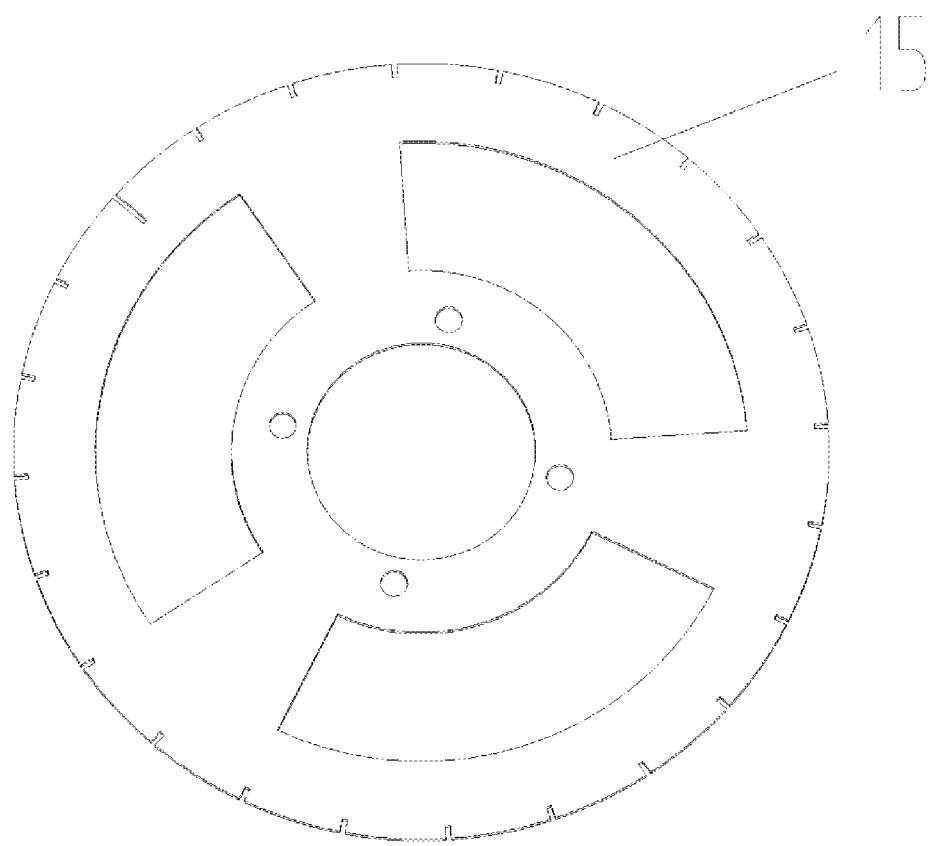
FIG. 4 is a structure schematic diagram of locating plate according to an embodiment of the present invention.

Further, the driving device further comprises: a second sensor 13 for detecting the position of the sample box holder, which is used for positioning of sample box holder 17 during rotation. Preferably, the second sensor 13 is U-type sensor, which is suitable for detecting the rotating position of sample box holder 17. Further, as shown in FIG. 1 and FIG. 4, a locating plate 15 is provided in the principal axis 3, the locating plate 15 is positioned above the big gear and match the U-type sensor as so to realize position of sample box holder 17 during rotation.

Further, the sample box holder further provides: a third sensor 4 for detecting whether the sample box is loaded into the sample box holder so as to ensure detection effect. The third sensor 4 is such as photoelectric sensor, which can detect rapidly.

Further, the rotating disc type fecal occult blood detection analyzer comprises: a base plate 20 for supporting whole detection devices and parts, for example, the sample box holder 17, driving device, pressing device and information collecting device are provided in the base plate. The base plate 20 is convenient for placing itself on plane such as desktop.

Further, the rotating disc type fecal occult blood detection analyzer further comprises: a controlling device is used for connecting the driving device, the pressing device and the information collecting device, and controlling rotation of sample box holder and collecting information. Further, the controlling device is programmable logic controller or integrated circuit plate. Thus structure is simple and easy to carry.

At the beginning, the sample box holder 17 rotates the first round, the sensor detects whether the sample box is loaded into the sample box holder. After that, the sample box holder 17 rotates the second round, the pressing lever presses each sample box one by one. In consider to reaction time between the diluent discharged from the sample box and strips after pressing so as to obtain adequate time for finishing the reaction and then obtain detection result, the sample box holder rotates another round, thus barcode scanning and photographing can be finished. The time is accurately controlled at 5 minutes from pressing the first sample box to collecting the information on the first sample box. The time is accurately controlled at 10 minutes from pressing the first sample box to collecting the information on the last sample box. Both the reaction time and detection speed be certain.

The primary advantages of rotating disc type fecal occult blood detection analyzer are as the follows: 1. Mechanism is simplified to the greatest extent, the structure of analyzer is simple and stability is increased. 2. Since the mechanism of analyzer is simplified, the volume thereof decreases, and the analyzer is more portable. 3. The transmission accuracy of the analyzer is increased by using of gear transmission, thus location is more accurate. 4. The sample boxes are accommodated in the sample box holder, which is be convenient for loading and unloading the sample boxes and be convenient for handling or recycling the medical waste. Meanwhile the problem that a sample box is overturned or toppled is effectively avoided by using of sample box holder.

The foregoing descriptions are merely specific schematic embodiments of the present invention, and are by no means intended to limit the scope thereof. All components of the present invention may be combined with each other if there is no conflict. Equivalent changes and modifications made by those skilled in the art without departing from the concept and principles of the present invention should fall within the scope of protection of the present invention.

What is claimed is:

1. A rotating disc type fecal occult blood detection analyzer used for detecting sample boxes, said sample box comprises a transparent sleeve, and a fecal collector and a test strip provided in the transparent sleeve, wherein said rotating disc type fecal occult blood detection analyzer comprises:
   a disc-shaped sample box holder carrying multiple sample boxes;
   a driving device for driving the sample box holder to rotate;
   a pressing device for pressing the sample boxes down; and
   an information collecting device for collecting color ribbon information presented on the test strips in the sample boxes and label information on the sample boxes.

2. The rotating disc type fecal occult blood detection analyzer according to claim 1, wherein said sample box holder can rotate about 360 degree, multiple clamping grooves for clamping or carrying sample boxes are provided in the bottom of said sample box holder, a open window for photographing and scanning the front and back of the sample box is provided above the side of said clamping grooves.

3. The rotating disc type fecal occult blood detection analyzer according to claim 1, wherein said driving device comprises: a driving motor for sample box holder, a gear set is connected to the driving motor for said sample box holder, and a principal axis is connected to the gear set, said sample box holder is connected to said principal axis.

4. The rotating disc type fecal occult blood detection analyzer according to claim 3, wherein said driving device further comprises: a second sensor for detecting said position of said sample box holder.

5. The rotating disc type fecal occult blood detection analyzer according to claim 3, wherein said sample box holder further provides: a third sensor for detecting whether said sample box is loaded into said sample box holder.

6. The rotating disc type fecal occult blood detection analyzer according to claim 1, wherein said pressing device comprises: stand, a driving motor for pressing is provided in said stand, a press lever is driven by said driving motor for pressing, and a cardinal axis is used for hinging said press lever to said stand.

7. The rotating disc type fecal occult blood detection analyzer according to claim 6, wherein said pressing device further comprises: a first sensor for detecting said position of said press lever.

8. The rotating disc type fecal occult blood detection analyzer according to claim 1, wherein said information collecting device comprises: a barcode scanning device is provided inside said sample box holder, and a camera is provided outside said sample box holder, said connecting line between said barcode scanning device and said camera is same as said radial direction of said sample box holder.

9. The rotating disc type fecal occult blood detection analyzer according to claim 1, wherein said rotating disc type fecal occult blood detection analyzer comprises: a base plate, said sample box holder, driving device, pressing device and information collecting device are provided in said base plate.

10. The rotating disc type fecal occult blood detection analyzer according to claim 1, wherein said rotating disc type fecal occult blood detection analyzer further comprises: a controlling device is used for connecting said driving device, said pressing device and said information collecting device.

* * * * *